(12) United States Patent
Bagchi et al.

(10) Patent No.: US 11,452,701 B2
(45) Date of Patent: Sep. 27, 2022

(54) TOPICAL EMULSION COMPOSITION CONTAINING NONSTEROIDAL ANTI-INFLAMMATORY DRUG

(71) Applicant: Johnson & Johnson Consumer Inc., Skillman, NJ (US)

(72) Inventors: Saumitra Bagchi, Princeton, NJ (US); Donald Hasenmayer, Eagleville, PA (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 159 days.

(21) Appl. No.: 16/202,614

(22) Filed: Nov. 28, 2018

(65) Prior Publication Data
US 2019/0167616 A1    Jun. 6, 2019

Related U.S. Application Data

(60) Provisional application No. 62/594,066, filed on Dec. 4, 2017.

(51) Int. Cl.
| | | |
|---|---|---|
| A61K 31/192 | (2006.01) | |
| A61K 9/107 | (2006.01) | |
| A61K 47/14 | (2017.01) | |
| A61K 9/00 | (2006.01) | |

(52) U.S. Cl.
CPC .......... *A61K 31/192* (2013.01); *A61K 9/0014* (2013.01); *A61K 9/107* (2013.01); *A61K 47/14* (2013.01)

(58) Field of Classification Search
CPC .... A61K 31/192; A61K 9/0014; A61K 47/14; A61K 9/107
See application file for complete search history.

(56) References Cited

U.S. PATENT DOCUMENTS

| | | |
|---|---|---|
| 4,543,251 A | 9/1985 | Kamishita |
| 5,210,099 A | 5/1993 | Mody et al. |
| 5,654,337 A | 8/1997 | Roentsch et al. |
| 5,811,111 A | 9/1998 | McAtee et al. |
| 8,343,962 B2 | 1/2013 | Kisak et al. |
| 8,728,514 B2 | 5/2014 | Choi et al. |
| 9,161,915 B2 | 10/2015 | Fossel |
| 9,205,041 B2 | 12/2015 | Chen et al. |
| 2005/0032900 A1 | 2/2005 | Krauser |
| 2007/0071688 A1 | 3/2007 | Illel et al. |
| 2011/0028460 A1 | 2/2011 | Kisak et al. |
| 2015/0141389 A1 | 5/2015 | Aliyar et al. |
| 2016/0303152 A1 | 10/2016 | Chandran |
| 2017/0296496 A1* | 10/2017 | Morrison ............. A61K 9/0014 |

FOREIGN PATENT DOCUMENTS

| | | |
|---|---|---|
| EP | 428352 A | 5/1991 |
| WO | WO 2002/078648 A | 10/2002 |
| WO | WO 2007/031753 A | 3/2007 |
| WO | WO 2007/070679 A | 6/2007 |
| WO | WO 2012/092528 A | 7/2012 |
| WO | WO 2014/084568 A | 6/2014 |

OTHER PUBLICATIONS

Makhmalzadeh et al., "Optimization of Ibuprofen Delivery through Rat Skin from Traditional and Novel Nanoemulsion Formulations", *Iranian Journal of Pharmaceutical Research* (2012) 11(1):47-58.
Mintel Database, Dolgit Krem Pain Relief Cream, Dolorgiet Arzneimittel company, Feb. 2006.
Mintel Database, Ibuleve Pain Relief Gel, DDD company, Nov. 2008.
Mintel Database, Ibuleve Speed Relief Gel, Diomed Developments company, Nov. 2017.
International search report and written opinion dated Feb. 20, 2019, for international application PCT/US2018/062764.
Baron, "A glance into the Book of Abstracts—Second International Congress on Neuropathic Pain (NeuPSIG)" European Journal of Pain 11(S1) 2007 vii-viii.
Bennett et al., "COX-2 inhibitors compared and contrasted", Expert Opinion Pharmacother 2001 2(11):1859-1876.
Campbell et al., "Mechanisms of Neuropathic Pain", Neuron, Author manuscript, 2007, pp. 1-31.
Kharkevich, Pharmacology, 3rd edition, Medicine 1987, pp. 47-48.
Kharkevich, Pharmacology, 10th edition, Publishing group, GEOTAR Media, 1987 pp. 73-74.
Vorobyeva, "The Role of Nonsteroidal Anti-inflammatory Drugs in the Treatment of Back Pain" Workbook, Specialist Advise, Journal of Research and Practice, Medicinskaya Kafedra 2005 3(15):136-143.
Zhulenko et al., Pharmacology 2008 pp. 34-35.

* cited by examiner

*Primary Examiner* — Kortney L. Klinkel
*Assistant Examiner* — Jason Deck

(57) ABSTRACT

In one aspect, the present invention features an emulsion composition including (i) at least 3%, by weight, of a nonsteroidal anti-inflammatory drug; (ii) at least 15%, by weight, of isopropyl myristate; (iii) at least 25%, by weight, of water; and (iv) one or more emulsifiers; wherein the formulation is substantially free of C1-C4 alcohols.

11 Claims, No Drawings

TOPICAL EMULSION COMPOSITION CONTAINING NONSTEROIDAL ANTI-INFLAMMATORY DRUG

CROSS-REFERENCE TO RELATED APPLICATIONS

This application claims the benefit of US provisional application 62/594,066 filed on Dec. 4, 2017, the complete disclosure of which is hereby incorporated herein by reference.

BACKGROUND OF THE INVENTION

Nonsteroidal anti-inflammatory drugs, such as ibuprofen, are commonly used to reduce pain, decrease fever, and decrease inflammation. While often administered orally, a number of topical NSAID-containing products are also sold, such as Voltaren™ gel, which contains diclofenac, and Ibuleve™ cream and Dolgit™ gel, both of which contain ibuprofen. These products are used to topically treat joint, bone, and/or muscle pain.

Other NSAID-containing compositions have been reported in the patent literature, such as: U.S. Pat. No. 9,161,915 to Strategic Sciences and Technologies LLC, which discloses a topical with ibuprofen and/or an ibuprofen salt and a nitric oxide donor; U.S. Pat. No. 9,205,041 to Aponia Laboratories, which discloses transdermal compositions containing ibuprofen or salts thereof and a gelling agent with isopropyl alcohol, isopropyl myristate and propylene glycol; and U.S. Patent Application No. 20050032900 to Krauser, which discloses and ibuprofen oil in water emulsion.

The present invention relates to a new NSAID-containing emulsion composition containing a high amount of isopropyl myristate that topically administers a high percent of the NSAID contained within the composition.

SUMMARY OF THE INVENTION

In one aspect, the present invention features an emulsion composition including (i) at least 3%, by weight, of a nonsteroidal anti-inflammatory drug; (ii) at least 15%, by weight, of isopropyl myristate; (iii) at least 25%, by weight, of water; and (iv) one or more emulsifiers; wherein the formulation is substantially free of C1-C4 alcohols.

In another aspect, the present invention features an composition including at least 3%, by weight, of a non-steroidal anti-inflammatory drug wherein: (i) less than 10% of the nonsteroidal anti-inflammatory drug has been converted to an ester following 30 days of accelerated stability; and (ii) the composition has an area under the curve of at least 5000 ng*hour/mL and a maximum concentration of at least 200 ng/mL when an amount of the composition containing 200 mg of the nonsteroidal anti-inflammatory drug is topically applied to a minipig.

In another aspect, the present invention features a method of treating pain, inflammation, or edema in a subject by topically applying to the subject such compositions. In one embodiment, such pain is selected from the group including joint, bone, ligament, tendon and muscle pain. In one embodiment, such pain is selected from the pain of osteoarthritis in joints, such as the knees and hands.

Other features and advantages of the present invention will be apparent from the detailed description of the invention and claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight (i.e., % W/W) unless otherwise specified.

Nonsteroidal Anti-inflammatory Drug

As discussed above, the emulsion composition includes a nonsteroidal anti-inflammatory drug ("NSAID"). NSAIDs are often classified based on their chemical structure or mechanism of action. Examples of NSAIDs include: salicylates such as aspirin, diflunisal, salicylic acid, and salsalate; propionic acid derivatives such as ibuprofen, dexibuprofen, naproxen, fenoprofen, ketoprofen, dexketoprofen, flurbiprofen, oxaprozin, and loxoprofen; acetic acid derivatives such as diclofenac, indomethacin, tolmetin, sulindac, etodolac, ketorolac, and aceclofenac; enolic acid derivatives such as piroxicam, meloxicam, tenoxicam, droxicam, lornoxicam, phenylbutazone, and droxicam; stereoisomers thereof; and salts thereof. In one embodiment, the NSAID is selected from the group including of ibuprofen, naproxen. ketoprofen, diclofenac, stereoisomers thereof, and salts thereof.

In one embodiment, the emulsion composition includes at least 1% by weight of one or more NSAIDs, such as at least 3%, such as at least 5%, such as at least 7%, and such as at least 10% by weight. In one embodiment, the emulsion composition includes up to 15% by weight of one or more NSAIDs, such as up to 10% by weight. In one embodiment, the emulsion composition includes at least 3%, such as at least 5%, and such as at least 7% by weight of ibuprofen, stereoisomers thereof, and salts thereof.

Emulsion Composition

The emulsion compositions useful in the present invention involve formulations suitable for topical application to skin. Examples of emulsion compositions include oil-in-water emulsions and water-in oil emulsions.

As discussed above, in one embodiment, the emulsion composition includes isopropyl myristate, water and one or more emulsifiers. In one embodiment, the emulsion composition includes at least 15% by weight of isopropyl myristate, such as at least 20% by weight of isopropyl myristate. In one embodiment, the emulsion composition includes from about 15% to about 50% by weight of isopropyl myristate. In one embodiment, the emulsion composition includes at least 25% by weight of water, such as at least 40% by weight of water. In one embodiment, the emulsion composition includes from about 15% to about 80% by weight of water. In one embodiment, the emulsion composition includes from about 0.5% to about 5% by weight, of one or more emulsifiers.

Examples of emulsifiers include: ethylene glycol stearates such as ethylene glycol palmitosterate and polyethylene glycol stearates (e.g., PEG-30 dipolyhydroxystearate, PEG-6 stearate, PEG-32 stearate, and PEG-100 stearate); glyceryl stearate; sorbitan stearate; diethylene glycol monoethyl ether; oleoyl polyoxylglycerides such as linoleoyl polyoxyl-6 glyceride; cetearyl glucoside; steareths such as steareth-2, steareth-20, steareth-21, steareth-25, and isosteareth-20; ceteths such as ceteth-2, cetheth-10 and ceteth-20; cetearehs such as ceteareth-20 and ceteareth-100; ceteths such as ceteths-1 and ceteth-45; polysorbates such as polysorbate-20, polysorbate-60, and polysorbate-80; lecithin, sorbitans such as sorbitan oleate, sorbitan monostearates, sorbitan stearate, and sorbitan isostearate; oleths such as oleth-2, oleth-10, and oleth-20; and laureths such as laureth-4.

In one embodiment, the emulsion composition further includes one or more thickeners. Examples of thickeners include acrylic acid polymer such as Carbomer 980 and acrylic/acrylamide polymers; gums such xanthan gum, gellan gum, and guar gum; glyceryl behenate; celluloses such as carboxymethyl celluloses, hydroxypropyl methylcelluloses, hydroxyethyl celluloses, hydroxypropyl celluloses, and methyl celluloses; poloxamers; collagens; gelatins; agar; carrageenans; pectin; polyethylenes; and polyvinyl alcohols.

The emulsion composition may further include one or more: chelating agents such as disodium EDTA; pH adjusters such as triethanolamine, diethylamine, octylamine, and diisopropanolamine; preservatives such as sodium benzoate; solubilizers for the NSAIDs such as propylene glycol; and emollients such as silicone fluid and cetyl alcohol.

In one embodiment, the emulsion composition has a pH range from 4-8, such as from 5-7. The methodology for testing pH of the emulsion composition can be tested as set forth below in Example 2.

Applicants found that some NSAIDs, such as ibuprofen, can form esters with certain alcohols. In one embodiment, the emulsion composition is substantially free of C1-C4 alcohols, such as methanol, ethanol, propyl alcohol, and isopropyl alcohol. In one embodiment, the emulsion composition is substantially free of C1-C16 alcohols, such as the above C1-C4 alcohols and fatty alcohols such as decanol, lauryl alcohol, myristyl alcohol, and cetyl alcohol. In one embodiment, the emulsion composition is substantially free of alcohols capable of esterifying the non-steroidal anti-inflammatory drug within the emulsion composition. What is meant by "substantially free" is in a concentration less than 5% by weight, such as less than 2%, such as less than 1%, such as less than 0.5%, such as 0% by weight (i.e. none).

Stability

In one embodiment, less than 10% (such as less than 5%, such as less than 1%) of the nonsteroidal anti-inflammatory drug has been converted to an ester following 30 days of accelerated stability, such as following 91 days of accelerated stability, such as following 182 days of accelerated stability. The methodology for testing the accelerated stability of the emulsion composition is set forth below in Example 2.

Bioavailability

In one embodiment, the emulsion composition has a plasma area under the curve ("AUC") of at least 5000, such as at least 7000, such as at least 9000 ng*hour/mL when an amount of the composition containing 200 mg of the non-steroidal anti-inflammatory drug is topically applied to a minipig. In one embodiment, the AUC of the emulsion composition when an amount of the composition containing 200 mg of the nonsteroidal anti-inflammatory drug is topically applied to a minipig is at least 5%, such as at least 7%, such as at least 9% of the AUC when 200 mg of the nonsteroidal anti-inflammatory drug is orally administered to a minipig.

In one embodiment, the emulsion composition has a maximum plasma concentration ("Cmax") of at least 200, such as at least 250, such as at least 300 ng/mL when an amount of the composition containing 200 mg of the non-steroidal anti-inflammatory drug is topically applied to a minipig. In one embodiment, the Cmax of the emulsion composition when an amount of the composition containing 200 mg of the nonsteroidal anti-inflammatory drug is topically applied to a minipig is at least 1%, such as at least 1.5%, such as at least 2% of the AUC when 200 mg of the nonsteroidal anti-inflammatory drug is orally administered to a minipig. The methodology for testing the AUC and Cmax of the emulsion composition is set forth below in Example 2.

EXAMPLE 1

Preparation of Emulsion Containing Ibuprofen without Propylene Glycol

An emulsion composition was manufactured using the following procedure and the materials in Table 1.

1. The isopropyl myristate, glyceryl behenate, PEG-6 stearate and ethylene glycol palmitostearate and PEG-32 stearate, linoleoyl Polyoxyl-6 glyceride, and ibuprofen were combined in a 4-oz clear jar equipped with a screw cap. These are considered the oil phase materials.
2. The sodium benzoate, disodium EDTA and purified water were combined in a separate 4-oz clear jar equipped with a screw cap. These are considered the water phase materials.
3. The jars from Steps 1 and 2 were placed into a hot water bath and heated until approximately 70° C.
4. The solid components dissolved into solution.
5. The water phase materials were removed and mixed using a high shear mixer and mixed for approximately 3 minutes. The Carbomer 980 was added and mixed for approximately 3 minutes.
6. While mixing, the oil phase materials were slowly poured into the water/Carbomer mixture and mixed using high energy for approximately 3 minutes.
7. The triethanolamine was added and mixed for 3 minutes.

TABLE 1

| Material | % W/W | Batch wt (100 g) |
|---|---|---|
| Ibuprofen | 7.5 | 7.5 |
| Isopropyl Myristate | 21.4 | 21.4 |
| Glyceryl Behenate[a] | 2.15 | 2.15 |
| PEG-6 Stearate and Ethylene Glycol Palmitostearate and PEG-32 Stearate[b] | 10.7 | 10.7 |
| Linoleoyl Polyoxyl-6 Glyceride[c] | 2.15 | 2.15 |
| Sodium Benzoate | 0.2 | 0.2 |
| Disodium EDTA | 0.1 | 0.1 |
| Carbomer 980[d] | 0.5 | 0.5 |
| Triethanolamine | 0.5 | 0.5 |
| Purified Water | 54.8 | 54.8 |
| TOTAL | 100 | 100 |

[a]Commercially available as Compritol ® 888 from Gattefosse, Inc.
[b]Commercially available as Tefose ® 63 from Gattefosse, Inc.
[c]Commercially available as Labrifil ® M2125 CS from Gattefosse, Inc.
[d]Commercially available as Lubrizol ® from Ashland, Inc.

The pH of the emulsion composition was calculated to be 6.01 by first adding and mixing equal amounts of deionized water and the emulsion composition prior to analysis.

EXAMPLE 2

In Vivo Minipig Study

The objective of this study was to evaluate pharmacokinetics of ibuprofen when given either orally or dermally as a single dose to minipigs. Topical samples (i.e., the three topical oil-in-water cream samples of Table 2 and the commercially available products Dolgit™ Cream (5% ibuprofen) and Ibuleve™ Cream (5% ibuprofen) were administered to the animals dermally for 36 hours (animals were rinsed following the last collection time point). The weight percent of each material of Samples 2a-2c are depicted in Table 3a. A similar mixing procedure used in Example 1 was used to prepare these samples. For samples including propylene glycol, cetyl alcohol, Polysorbate 80, Transcutol HP™, or Labrasol™, they were included with the oil phase materials. For samples containing silicone fluid, it was mixed into the main emulsion at the end at high speed for approximately 3 minutes until completely blended. For samples containing diethylamine, it was added along with the triethanolamine.

The pHs of the emulsion compositions were calculated to be 6.77 (Sample 2a), 5.7 (Sample 2b), and 6.65 (Sample 2c) by first adding and mixing equal amounts of deionized water and the emulsion composition prior to analysis.

The dorsal surfaces of the animals were prepared by close clipping of the hair with a small animal clipper prior to the dosing. Care was taken during the clipping procedure to avoid abrasion of the skin. The samples were applied directly to the skin in a uniform layer over each designated area by gentle inunction with a disposable plastic applicator. A target area of 400 cm² was covered with a thin, uniform film of the appropriate sample. Samples 2a-2c were dosed at 2.67 g (i.e., 200 mg of ibuprofen) and Ibuleve™ and Dolgit™ were both dosed a 4 g (i.e., 200 mg of ibuprofen). All animals had intact skin. The corners of the application site were marked with indelible ink to allow proper identification of the treated and untreated skin as often as needed. Residual test material was removed following the appropriate exposure time by gently wiping the site with gauze soaked in reverse osmosis water, followed by dry gauze.

TABLE 2

| Material | Sample 2a % W/W | Sample 2b % W/W | Sample 2c % W/W |
|---|---|---|---|
| Ibuprofen | 7.5 | 7.5 | 7.5 |
| Propylene Glycol | 5 | 5 | 5 |
| Isopropyl Myristate | 20 | 20 | 20 |
| Glyceryl Behenate | 2 | 0 | 2 |
| Polysorbate 80 | 0 | 4 | 4 |
| PEG-6 Stearate and Ethylene Glycol Pairnitostearate and PEG-32 Stearate | 10 | 8 | 8 |
| diethylene glycol monoethyl ether[a] | 0 | 1.4 | 1.4 |
| Cetyl Alcohol | 0 | 2 | 0 |
| Caprylocaproyl polyoxyl-8 glycerides[b] | 0 | 0 | 0 |
| Linoleoyl Polyoxyl-6 Glyceride | 2 | 0 | 0 |
| Diethylamine | 1 | 0 | 1 |
| Purified Water | 50.2 | 48.8 | 47.8 |
| Sodium Benzoate | 0.2 | 0.2 | 0.2 |
| Disodium EDTA | 0.1 | 0.1 | 0.1 |
| Silicone Fluid[c] | 0 | 1 | 1 |
| Carbomer 980 | 1 | 1 | 1 |
| Triethanolamine | 1 | 1 | 1 |

[a]Commercially available as Transcutol HP ™ from Gattefosse, Inc.
[b]Commercially available as Labrasol ™ from Gattefosse, Inc.
[c]Commercially available as Dow Corning ™ Q7-9120 from Dow Corning An oral tablet of 200 mg ibuprofen (Motrin™ IB) was also administered to the animals by use of a "pill gun." The tablet was placed into the split rubber tip of the "pill gun," and the mouth of the animal was opened. The tip was placed towards the back of the mouth over the hump of the tongue and the tablet was expressed by depressing the plunger. Once the tablet was administered, each dose was followed by a reverse osmosis water flush to encourage swallowing.

Each of the topical and oral test samples were tested on four minipigs, and the results of the study are depicted below in Table 3a.

TABLE 3a

| Test Sample | Maximum Concentration (Cmax) [ng/mL][a] | Area Under the Curve (AUC) [ng * hour/mL][b] | Tmax [hours][c] | % Relative to Bioavailability of Oral Ibuprofen | Fold Difference in Cmax of Ibuleve ™ | Fold Difference in AUC of Ibuleve ™ |
|---|---|---|---|---|---|---|
| Ibuleve ™ | 133.25 (27.5) | 3905.33 (24.4) | 8 (4-24) | 4.08 | — | — |
| Dolgit ™ | 64.23 (16.1) | 1106.67 (24.2) | 18 (12-24) | 1.16 | 0.48 | 0.28 |
| Sample 2a | 349.5 (42.8) | 9953.87 (35.9) | 16 (2-24) | 10.39 | 2.62 | 2.55 |
| Sample 2b | 344 (29.8) | 9362.82 (25) | 24 (24-24) | 9.77 | 2.58 | 2.40 |
| Sample 2c | 359 (37.1) | 9511.32 (35.2) | 12 (12-24) | 9.93 | 2.69 | 2.43 |
| Oral Ibuprofen | 13862.5 (55.2) | 95807.8 (20.8) | 4 (2-4) | — | — | — |

[a]Number in parenthesis is the standard error
[b]Number in parenthesis is the standard error
[c]Number in parenthesis is the range of Tmax As is indicated in Table 3a, Samples 2a-2c all unexpectedly had superior Cmax, AUC, and relative bioavailability as compared to either Ibuleve™ or Dolgit™. For example, Sample 2a had a 2.62 times greater Cmax and a 2.55 times greater AUC than Ibuleve™.

Samples 2a-2c were also tested for under accelerated stability conditions to determine the amount of ibuprofen ester formation. Approximately 1 oz of the samples were stored for 3 months (91 days) in glass jars with lids in a laboratory oven maintained at 40° C. The results are depicted below in Table 3b (values are the percent of ibuprofen converted to the listed ester). To conduct the accelerated stability analysis, a high-performance liquid chromatograph (HPLC) was equipped with a Waters UPLC C18, 2.1 ID×50 mm, held at 40° C., 1.7 µm particle size column, and a mobile phase gradient of 0.1% trifluoroacetic acid in water and 0.1% trifluoroacetic acid in acetonitrile where the mobile phase is changed at ratios of 95:5 to 5:95 over 8 minutes. A flow rate of 0.65 mL/min and an injection volume of 0.2 µL was used, and the UV detector was set at a wavelength of 264 nm.

TABLE 3b

| Ester | Sample 2a | Sample 2b | Sample 2c |
|---|---|---|---|
| Ibuprofen-diethylene glycol monoethyl ether | ND | 0.49 | 0.34 |
| Ibuprofen-cetyl alcohol | ND | 3.97 | ND |
| Ibuprofen-propylene glycol | 0.65 | 0.86 | 0.61 |

ND = none detected

The above results confirm that ibuprofen will form an ester with the alcohols diethylene glycol monoethyl ether, cetyl alcohol, and propylene glycol. Of note, Samples 2a and 2c were found to have a lower conversion of ibuprofen to the ibuprofen-propylene glycol ester then Sample 2b, which Applicants believe is due to the presence of the lipophilic pH adjuster diethylamine.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. An emulsion composition comprising:
   (i) at least 7%, by weight, of a nonsteroidal anti-inflammatory drug;
   (ii) at least 15%, by weight, of isopropyl myristate;
   (iii) at least 25%, by weight, of water;
   (iv) one or more emulsifiers;
   (v) one or more pH adjusters; and
   (vi) one or more solubilizers,
   wherein the one or more pH adjusters comprises diethylamine,
   wherein the one or more solubilizers comprises propylene glycol,
   wherein said composition contains less than 5% by weight of C1-C16 alcohols, and
   wherein said nonsteroidal anti-inflammatory drug is selected from the group consisting of ibuprofen, stereoisomers thereof, and salts thereof.

2. A composition of claim 1, wherein said composition comprises at least 20%, by weight, of said isopropyl myristate.

3. A composition of claim 1, wherein said composition comprises at least 40%, by weight, of said water.

4. A compound of claim 1, wherein said one or more emulsifiers is ethylene glycol stearate.

5. A composition of claim 1, wherein said composition contains less than 5% by weight of alcohols capable of esterifying said non-steroidal anti-inflammatory drug.

6. A composition of claim 1, wherein less than 10% of said nonsteroidal anti-inflammatory drug has been converted to an ester following 30 days of storage of the composition in a glass jar with a lid in a laboratory oven maintained at 40° C.

7. A composition of claim 1, wherein said composition has a plasma area under the curve of at least 5000 ng*hour/mL when an amount of said composition containing 200 mg of said nonsteroidal anti-inflammatory drug is topically applied to a minipig.

8. A composition of claim 1, wherein said composition has a maximum plasma concentration of at least 200 ng/mL when an amount of the composition containing 200 mg of the nonsteroidal anti-inflammatory drug is topically applied to a minipig.

9. An emulsion composition of claim 1, wherein:
   (i) less than 10% of said nonsteroidal anti-inflammatory drug has been converted to an ester following 30 days of storage of the composition in a glass jar with a lid in a laboratory oven maintained at 40° C.; and
   (ii) said composition has a plasma area under the curve of at least 5000 ng*hour/mL and a maximum plasma concentration of at least 200 ng/mL when an amount of said composition containing 200 mg of said nonsteroidal anti-inflammatory drug is topically applied to a minipig.

10. A composition of claim 1, wherein said one or more pH adjusters further comprises at least one of triethanolamine, octylamine, and diisopropanolamine.

11. A method of treating pain in a subject, said method comprising topically applying to said subject a composition of claim 1.

* * * * *